United States Patent
Vijay et al.

(10) Patent No.: US 7,160,866 B2
(45) Date of Patent: Jan. 9, 2007

(54) **ISOLATION OF TIGOGENIN PENTAGLYCOSIDE FROM *CHLOROPHYTUM NIMONII***

(75) Inventors: Lakshmi Vijay, Lucknow (IN); Kartikay Pandey, Lucknow (IN); Raja Roy, Lucknow (IN); Bhawani Shankar Joshi, Lucknow (IN); Padmanabhan Madhusudanan Kunnath, Lucknow (IN); Ramesh Chandra, Lucknow (IN); Arvind Kumar Srivastava, Lucknow (IN); Deepak Raina, Lucknow (IN); Anil Kumar Rastogi, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 369 days.

(21) Appl. No.: 10/806,065

(22) Filed: Mar. 22, 2004

(65) Prior Publication Data

US 2005/0209168 A1   Sep. 22, 2005

(51) Int. Cl.
*A61K 31/70* (2006.01)
*C07H 1/06* (2006.01)
*C07J 41/00* (2006.01)

(52) U.S. Cl. .............................. 514/26; 536/5; 536/128
(58) Field of Classification Search ................... 536/5, 536/128; 514/26
See application file for complete search history.

(56) References Cited

U.S. PATENT DOCUMENTS

| 3,303,187 A | 2/1967 | Rubin |
| 4,602,003 A | 7/1986 | Malinow |
| 5,591,836 A | 1/1997 | Mazur et al. |

FOREIGN PATENT DOCUMENTS

| EP | 0159431 | 10/1985 |
| WO | 95/00018 | 1/1995 |

OTHER PUBLICATIONS

Mimaki, Y., et al., "Steroidal saponing from the underground parts of chlorophytum comosum and their inhibitory activity on tumor promoter-induced phospholipids metabolism of HeLa cells" PHYTOCHEMISTRY, vol. 41, No. 5, pp. 1405-1410 (1996).

*Primary Examiner*—Elli Peselev
(74) *Attorney, Agent, or Firm*—Ladas and Parry LLP

(57) ABSTRACT

The present invention provides a novel saponin tigogenin penta glycoside isolated from the aerial parts of *Chlorophytum nimonii* and a process for the isolation thereof as well as its use in anti-hyperglycemic and hypolipidemic activities.

11 Claims, No Drawings

ISOLATION OF TIGOGENIN PENTAGLYCOSIDE FROM *CHLOROPHYTUM NIMONII*

FIELD OF THE INVENTION

The present invention provides a novel saponin tigogenin penta glycoside isolated from the aerial parts of *Chlorophytum nimonii*. The present invention also provides a process for the isolation of new saponin Tigogenin penta glycoside from the aerial part of the *Chlorophytum nimonii* (Grah) Dalz in Hook and its new potent anti-hyperglycemic and hypolipidemic activities.

BACKGROUND OF THE INVENTION

The genus *Chlorophytum* Ker-Gawl (Family *Liliaceae*) is known by about 200 species and is distributed mainly in tropical and subtropical countries. It is represented in India by about 15 species, which occur mostly in peninsular India. Most of the species are herbs with short root stock fascieled roots often thick, fleshy and tuberous.

*Chlorophytum nimonii* (Grah) Dalz. in Hook. Kew J. Bot. 2:142,1850 (Syns. *Antherium nimonii* Grah.; *Chlorophytum orchidastrum* sensu Baker non Lindl.), a herb upto a meter tall. Root fibres tuberous, leaves 5–10 mm thin, elliptic-lanceolate, acute, 30–60 cm. long, 1.5–10 cm. broad, strongly nerved, glabrous and shining on both sides, narrowed at base into a winged petiole 15–25 cm. long scape 20–40 cm. long thick, terete. Flowers are very small, white in very lax panicles 30–60 cm. long with ovate-lanceolate, bracts 0.2–3.5 cm; Perianth 6, very small 3–10×2–5 mm. Subacute, 5-nerved. Stamens 6, hypoglymous, about 5 mm. long. Capsule 6×3 mm., depressed, globose deeply lobed at the apex, transversely veined. Seed solitary, flattened, orbicular, minutely pappillose, dull black. Flowering and fruiting period ranges between May-August. It is also occasionally and infrequently distributed in South India [Hooker, J. D.; (1894)], *Chlorophytum* Ker. *Flora of British India*, Vol. 6 pp 333–335. L. Reeve and Co., London.; Cooke, T. (1908) *Chlorophytum* Ker., *Flora of the Presidency of Bombay*, Vol. 3, pp 280–283. Rep. Ed. (1958), BSI, Calcutta.; Fischer, C. E. C, (1928), *Chlorophytum* In Ker. J. S. Gamble, *Flora of the Presidency of Madras*, Vol. 3, pp 1064–1066 Rep. Ed. (1967), BSI, Calcutta; Santapan, H and Henry, A. N [1973], *A Dictionary of The Flowering Plants in India* pp 38, CSIR publication, New Delhi; Karthikeyan, S., Jain, S. K., Nayer, M. P. and Sanjappa, M [1989] Flora Indicae Enumerato; Monocotyledonae, pp 91–92, BSI, Calcutta].

*Chlorophytum arundinaceum* Baker, root powder after frying in ghee, is used for chewing in case of aphthae in mouth and throat [Asolkar, L., Kakkar, K. K. Chakre, O. J. In "*Second suppliment to glossary of Indian Medicinal Plants with Active Principle* P-197(1992) PID, New Delhi], Roots of other species *Chlorophytum tuberosum* [Roxb] Baker is used as vegetable tonic. No chemical or biological studies have been reported on *Chlorophytum nimonii* in literature. However, from other species, saponins, sapogenins, phenolic compounds, sugars, fatty acids and polysaccharides have been isolated and reported in literature.

OBJECTS OF THE INVENTION

The main object of the invention is to provide a novel saponin from the aerial parts of *Chlorophytum nimonii*, which is useful for its anti-hyperglycemic and hypolipidemic activity.

SUMMARY OF THE INVENTION

Accordingly, the present invention provides a novel saponin tigogenin pentaglycoside of formula I below isolated from aerial parts of *Chlorophytum nimonii*

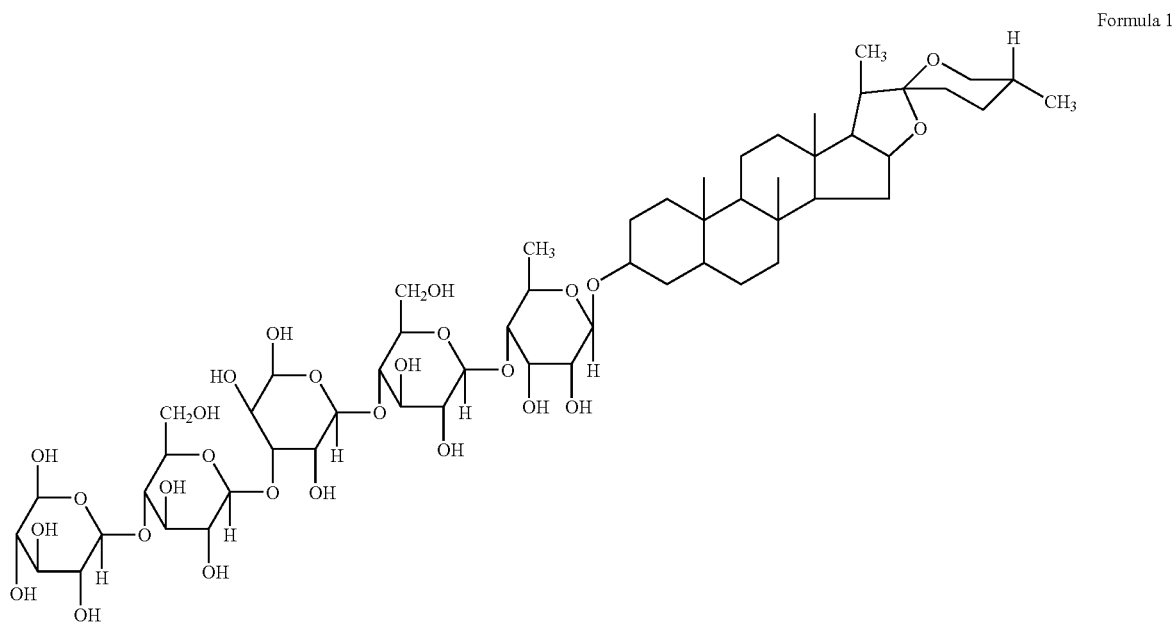

Formula 1

The present invention also provides a process for the isolation of a new saponin Tigogenin pentaglycoside of formula I below from the aerial part of the *Chlorophytum nimonii* (Grah) Dalz in Hook which process comprises (i) soaking material comprising dried and chopped aerial parts of *Chlorophytum nimonii* in a polar solvent at a temperature in the range of 25 to 30° C. to obtain an (ii) filtering the extract, followed by removal of the polar solvent until dryness under vacuo to obtain the compound of formula; and (iii) purifying the compound of formula 1

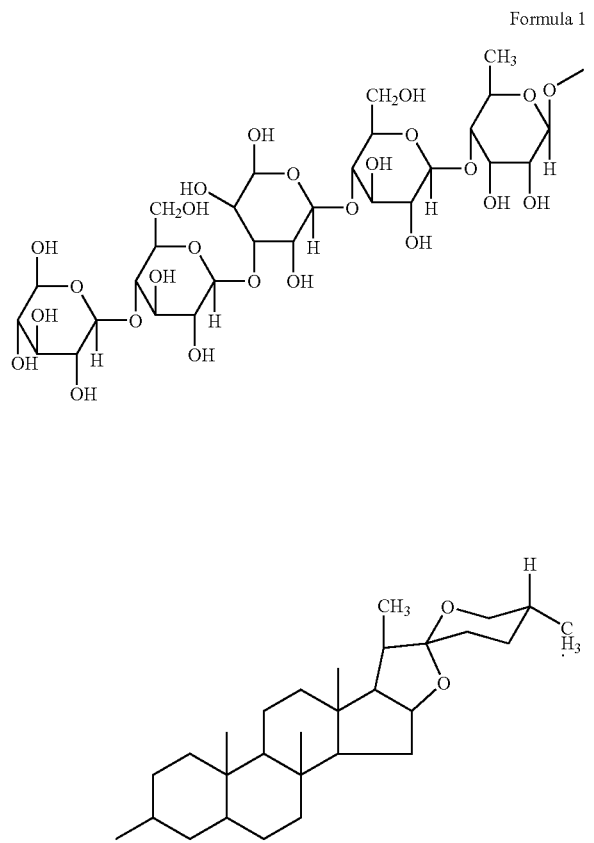

Formula 1

In one embodiment of the invention, the polar solvent used is selected from the group consisting of butanol, methanol, ethanol, water and any mixture thereof.

In another embodiment of the invention, the dried and chopped aerial parts of *Chlorophytum nimonii* is soaked repeated for up to 4 to 5 times in the polar solvent.

In another embodiment of the invention, the soaking is carried on for a period of about 24 hours.

In another embodiment of the invention, the filtrate is concentrated to 300 ml under reduced pressure below 50° C.

In another embodiment of the invention, the polar solvent used is 95% ethanol.

In yet another embodiment of the invention, the extract obtained at the end of step (ii) is subjected to fractionation into four fractions comprising hexane soluble fraction, n-butanol soluble fraction, chloroform soluble fraction and n-butanol insoluble fraction.

The present invention also relates to a pharmaceutical composition comprising a pharmaceutically effective amount of a compound of formula 1 above and one or more pharmaceutically acceptable additives.

In one embodiment of the invention, the pharmaceutically effective amount of compound of formula 1 is in the range of 100 to 500 mg/kg of body weight of a patient.

The present invention also provides the use of compound of formula 1 in the treatment of diabetes and hyperlipidemia.

DETAILED DESCRIPTION OF THE INVENTION

Isolation of saponin and other compounds are reported by conventional methods e.g. (Column chromatography, Fractionation etc. and are of only academic interest. Tandon, M and Shukla, Y. N. J. Indian Chem. Soc. (1992) 69, 893; Tandon, M., Shukla, Y. N. and Thakur, R. S. *Phytochemistry*, (1992) 31, 2525; Gupta. R., Gupta, O. C. D., Gupta. P. C. and Pande, C. S., *Planta Med*. (1979), 37(1), 94–5; Tandon, M. and Shukla Y. N., *Indian J Chem*., (1996) Sec. B (9), 988–989. Tandon. M. & Shukla, Y. N., *Phytochemistry* [1993], 32(6) 1624–5). Literature search on biological activity on *Chlorophytum* species, revealed only inhibitory activity on Tumor prohibitory induced phospholipid metabolism of the Hela cells by the saponins isolated from *C. cosmosum* (Yoshihiro, M. Toshihiro, K. Yutaka, S., Atsuku, N, Yashiko, S and Hoyoku Holjaku, N., *Phytochemistry*, (1996) 41(5), 1405–10; Xingcong, Li, Dezu, W. and Chongren. Y., *Phytochemistry*, (1990), 29 (12), 38899–901]. The present invention relates to "A process for the isolation of new saponin Tigogenin penta glycoside from the aerial part of the *Chlorophytum nimonii* (Grah) Dalz in Hook and its potent antihyperglycemic and hypolipidemic activities".

Air-dried powdered of the aerial portion of the plant was soaked in 95% ethanol at room temperature and the first ethanolic extract was taken out after 24 hours. The process of extraction was repeated 4–5 times and combined extract after filtration was concentrated to 300 ml under reduced pressure below 50° C. On keeping the concentrated extract in refrigerator for over night, beautiful shining white crystals appeared at the bottom of the flask, which were filtered out and washed with ethanol. On purification these crystals were found giving our required saponin coded K014. The filtrate was concentrated up to a residual green viscous mass, which was coded as D002. A part of the filtrate (D002) was fractionated into four fractions i.e. hexane (F003), chloroform (F004), n-butanol soluble (F005) and n-butanol insoluble (F006) fractions. All these fractions and crude extracts were evaluated for hypolipidemic and antihyperglycemic activities. n-butanol soluble fraction on purification yielded the pure saponin [K007 Yield=10%, which was evaluated for antihyperglycemic and hypolipidemic activities. Structure of the saponin was determined by physiochemical technique as Tigogenin penta glycoside as below:
Tigogenin-3-O-α-L-rhamnopyranosyl-1-3-β-D-xylopyranosyl-1→4-β-D-glucopyranosyl-1-3-β-D-xylopyranosyl-1→4-β-D glucopyranoside (1).

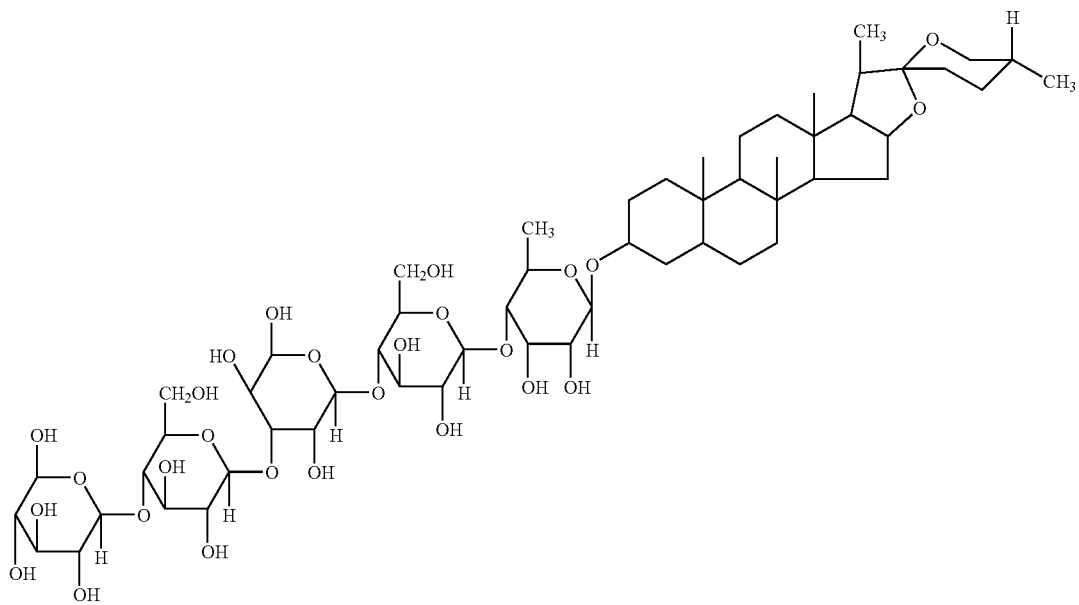

Antihyperglycaemic Activity Evaluation:

A. In Sucrose Loaded Rat Model

Normal Charles Foster strains of albino rats (140–180 g body weight) were procured from the animal colony of Central Drug Research Institute, Lucknow. Animals showing blood glucose between 60 to 80 mg/dl (3.33 to 4.44 mM) were divided into groups of five to six animals in each. Rats of experimental groups were administered suspension of the desired sample orally (made in 1.0% Gum acacia) at an arbitrary dose of 250, 100 and 100 mg/kg body weight, respectively, for crude extract, fractions and pure compounds. Animals of control group were given an equal amount of 1.0% gum acacia. A sucrose load (10.0 g/kg) was given to each animal orally exactly after 30 min post administration of the test sample/vehicle. Blood glucose profile of each rat was again determined at 30, 60, 90 and 120 min post administration of sucrose by glucostrips (Boehringer, Mannheim (Germany). Food but not water was withheld from the cages during the course of experimentation. Quantitative glucose tolerance of each animal was calculated by area under curve (AUC) method. Comparing the AUC of experimental and control groups determined the percentage lowering on post prandial hyperglycaemia. Samples showing significant ($p<0.05$) inhibition on post prandial hyperglycaemia were considered as antihyperglycaemic samples.

B. In Streptozotocin-Induced Diabetic Rats

Charles Foster strains of albino rats were selected for this study. Rats of body weight 140±20 g were finally taken. Streptozotocin (Sigma, USA) was dissolved in 100 mM citrate buffer (pH 4.5) just before giving the injection and calculated amount of STZ solution was injected to overnight fasted rats (60 mg/kg) intraperitoneally. Blood was checked 48 h later by Glucometer (Boehringer Manheim (Germany) and animals showing blood glucose profiles of over 250 mg/dl were considered as diabetic. The diabetic animals were again divided into groups of six animals in each and their blood glucose profiles were again checked on the day of experiment (Day 3). Rats showing almost equal or similar value of blood glucose profile were divided again into groups consisting of 5–6 animals in each. Rats of experimental groups were administered suspension of the desired test sample orally (made in 1% Gum acacia) at 250 or 100 mg/kg body weight depending on the nature of the sample. Animals of group I (control) were given an equal amount of 1% Gum acacia. Blood glucose level of each rat was again determined at 1, 2, 3, 4, 5, 6, 7 and 24 hours, respectively post administration of test sample/vehicle. Food but not water was withheld from the cages during the experimentation. The % fall of blood glucose level by the test substance was calculated according to the following formula:

$$\% \text{ Antihyperglycaemic Activity} = 100 - \frac{\text{Average blood glucose level of the test substances treated group at test time} \times 100}{\text{Average blood glucose level of control group at test time}}$$

Results of the antihyperglycaemic activity of crude extract (D002) and fractions of D002 i.e. F003 to F006 in glucose loaded rat model were presented in Table 1. It is evident from the results that the crude extract (D002) and the three fractions i.e. hexane (F003), chloroform (F004) and butanol-soluble (F005) fractions lowers the rise in post prandial hyperglycaemia post sucrose load. The average lowering were calculated to be around 51, 41, 34 and 50%, respectively. The pure compound i.e. Tigonenin penta glycoside (K007) showed an average of 23% fall on blood glucose profile of streptozotocin-induced diabetic rats.

TABLE 1

Antihyperglycaemic activity in crude extract, fractions and pure compound of *Chlorophytum nimoni*

| S. No. | No. of extract./fractions./ pure compound | Dose (mg/kg) | % Activity in GLM model | % Activity in STZ model | Significance |
|---|---|---|---|---|---|
| 1 | D002 (Ethanolic extract) | 250 | 51 | | $P < 0.05$ |
| 2 | F003 (Hexane fraction) | 100 | 41 | | $P < 0.05$ |
| 3 | F004 (Chloroform fraction) | 100 | 34 | | $P < 0.05$ |
| 4 | F005(n-Butanol sol. Fraction) | 100 | 50 | | $P < 0.05$ |
| 5 | F006n-butanol insoluble fraction) | 100 | 0 | | |
| 6 | K007 (saponin) | 100 | 64 | 23 | $P < 0.05$ |

Hypolipidaemic Activity Evaluation:

A. Triton model

The lipid lowering activity of this plant saponin [K007] was evaluated in triton induced hyperglycemic rats. However, lipid as well as glucose lowering action of compound was assessed in dyslipidemic hamster model. Male Charles Foster rats weighing 200–225 g were divided into control, hyperlipidemic and hyperlipidemic plus drug treated groups containing six animals in each group. Hyperlipidemia was induced by administration of Triton WR-1339 [200 mg/kg i.p.]. All animals were maintained on standard pellet diet and water ad-libitum. Saponin [K007] and standard drug "Guggalipid" were macerated with 2% aqueous gum acacia suspension. The suspension was fed orally to the desired group at the dose of 100 mg/kg simultaneously with Triton WR-1339 in drug treated group. The animals of control group received same amount of gum acacia suspension. At the end of experiment, after 18 hours blood was withdrawn from the retro orbital plexus and plasma was used for assay of the total cholesterol [Enzymatic Determination of blood Cholesterol-by Diagnostic code No. 1489232 (CHOD-PAP) supplied by Boehringer Mannheim], phospholipid (Phosphorous-lipid Assay Kit code No. 124574 supplied by Boehringer Mannheim Gmbh, Germany) and triglyceride [Plasma triglyceride Assay Kit Engymatic determination code No. 701904, GOP-PAP, supplied by Boehringer Mannhein Gmbh, Germany]. The results have been tabulated in Table-2.

B. Dyslipidaemic Hamster Model

Male golden Syrian hamster weighing 100–120 g. was divided into control dyslipidemic plus drug treated groups of six animals each. Dyslipidemia was produced by feeding with high fat diet [HFD] made-up of a mixture of normal hamster pellet diet (700 g). Cholesterol (5.0 g). Deoxycholic acid (5.0 g). Fructose (100 g). and Coconut oil 300 g. Dyslipidemic hamsters had free access to HFD and water through out experiment for 14 days (two weeks). Saponin (K007) was macerated with 2% aqueous gum acacia and fed orally at a dose of 345 mg/kg p.o. from day 8 to day 14 (7 days) in dyslipidemic plus drug treated group. Control animals, maintained on normal pellet diet and water were simultaneously fed with same amount of gum acacia suspension. At the end experiment on $14^{th}$ day body weight of individual animal was taken and their non fasted blood was withdrawn, sacrificed, the liver was excised and weighted, plasma was prepared and assayed for glycerol [Enzymatic Assay Kit For Glycerol—Code No.-337 (GPO-Trinder supplied by Sigma Chem. Co. USA)] Glucose [Enzymatic assay kit for Glycerol code No. 337 (GPO-Trinder) supplied by Sigma Chem. Co. USA]. However, cholesterol Tg was assayed using diagnostic kits as described for Triton model. The results are presented in Table. 3. In another set of experiment dyslipidemia in hamster was produced by feeding with HFD coded D 99122211 supplied by Nova-Nordisk Pharmaceuticals. Denmark. Saponin [K007] was fed at the time of doses (345 mg) 300 µmole/kg/p.o. A few additional biochemical parameter such as HDL-Tc [High density lipoprotein, Code No. 543004 supplied by Boehringer Mannheim Gmbh Germany], Free Fatty acids (micro determination of free fatty acids, Dole V. P. *J Lipid Research*, 6 151-157(1965)] were assayed in plasma and the results are presented in Table 4.

TABLE 2

Hypolipidaemic Effect of pure compound Tigonenin penta glycoside (K007) in Triton treated rats.

| Treatment (Dose mg/kg) | Total Cholesterol | Phospholipid | Triglyceride |
|---|---|---|---|
| Control | 87.5 ± 13 | 76.8 ± 14 | 90.0 ± 13 |
| Triton | 466.9 ± 90 | 318.5 ± 21 | 268.0 ± 20 |
| Triton + saponin (K007) (100 mg/kg) | 345.7 ± 27* (26) | 239.9 ± 40* (25) | 208.5 ± 31* (22) |
| Triton + guggulipid (100 mg/kg) | 307.9 ± 88 (34) | 201.8 ± 32 (37) | 177.5 ± 29 (34) |

Values expressed as mg/dl are the mean ± SD of 6 rats. Values in the parentheses are percent decrease in triton-drug treated group compared to triton-treated group. Significance: $p < 0.001$ except marked with asterisk *$p < 0.01$.

TABLE 3

Effect of pure compound Tigonenin penta glycoside (K007) on plasma lipid profiles of dyslipidemic hamsters

| Treatment | Total Cholesterol | Triglycerides | Glucose |
|---|---|---|---|
| Control | 126.4 ± 12 | 64.6 ± 4 | 86.0 ± 12 |
| HFD | 310.1 ± 8 | 278.7 ± 3 | 112.5 ± 12 |
| HFD + saponin(K007) (345 mg/kg) | 237.7 ± 7 (23) | 220.6 ± 5 (5) | 96.5 ± 10 (14) |
| HFD + guggul lipid (250 mg/kg) | 218.5 ± 5 (30) | 204.5 ± 5 (27) | 109.2 ± 16 |

Values expressed as mg/dl are the mean ± SD of 6 hamsters. Values in the parenthesis are percent decrease as compound to HFD group.

TABLE 4

Effect of pure compound Tigonenin penta glycoside (K007) on plasma lipid profiles in dyslipidemic hamsters

| Treatment | Triglyceride (Tg) | Total Cholesterol (Tc) | HDL Cholesterol | Glucose (Glu) | Glycerol (Gly) | Free fatty acids (FFA) |
|---|---|---|---|---|---|---|
| Control | 145 ± 15 | 108 ± 20 | 36 ± 4 | 105 ± 18 | 70 ± 11 | 40 ± 7 |
| HFD | 539 ± 70 | 466 ± 55 | 45 ± 6 | 136 ± 20 | 92 ± 15 | 126 ± 13 |
| HFD + saponin (K007) dose-345 mg/kg (300 µmole) | 261 ± 11 (−52) | 172 ± 90 (−63) | 52 ± 3 (+53) | 78 ± 10 (−42) | 64 ± 3 (−30) | 84 ± 6 (−33) |

Values expressed as mg/dl are the mean ± SD of 6 hamsters. Values in parentheses are percent change as compared to HFD group.

Values expressed as mg/dl are the mean±SD of 6 hamsters. Values in parentheses are percent change as compared to HFD group.

Data in the Table-2 showed that administration of triton WR-1337 in rats caused increase in their plasma Tc, PL and Tg levels by 5.33, 4.14 and 2.91 folds, respectively. Treatment with saponin (K007) caused significant lowering in plasma lipid levels of triton plus drug treated group, however, these effects were of low order than guggul lipid. Feeding with HFD in hamsters caused dyslipidemia which was reflected in increased levels of plasma Tc (2.45 fold), Tg (4.3 fold) and glucose (30%) respectively. Treatment with saponin (K007) caused lowering in plasma levels of Tc, Tg and glucose by 23, 21 and 14% respectively. At the same time the standard lipid lowering drug; guggul lipid exerted more lipid lowering action but did not effect the increased level of glucose in dyslipidemic hamsters (Table 3). Investigations on the effect of saponin (K007) were also made on the dyslipidemia induced in hamster fed with HFD-D-99122211 supplied by Novo-Nordisk, Denmark. Feeding with HFD caused marked increase in the level of blood glucose. Feeding of high fat diet D-9912211 to hamsters caused marked increase in plasma Tg, Tc, FFA levels by 3.7, 4.3 and 3.1 folds, respectively accompanied by increase in HDL, glucose and glycerol by 25, 30 and 31% respectively. Treatment with K007 at a dose of 345 mg/kg/p.o. significantly reversed the plasma levels of Tg,Tc,glu, glycerol and FFA by 52, 63, 42, 30 and 33%, respectively in dyslipidemic plus drug treated animals without causing any adverse effect on plasma HDL (Table-4).

In conclusion, compound 3964-saponin (K007) has potent hypolipidaemic activity together with antihyperglycaemic activity in validated animal models. This compound has also favourable effects on HDL-cholesterol levels in animals.

EXAMPLE-1

Aerial part of *Chlorophytum-nimonii* (100 g) was air dried, powdered and soaked in methanol (5 times in 200 ml). All the methanolic extracts were decanted, mixed, filtered and evaporated to dryness. The dried residue was dissolved again in methanol (5 times in 100 ml) to filter out the methanol insoluble inorganic salts. The greenish residue thus obtained was successively macerated with chloroform and n-butanol. The chloroform fraction was rejected and n-butanol fraction after removal/recovery of most of the n-butanol was evaporated to dryness. The dried residue was dissolved into methanol (100 ml). To it 200 ml of acetone was added gradually with stirring. The light brown precipitate that separated out was filtered. The dried powder was again dissolved in methanol (50 ml) and 100 ml acetone was added to get colourless or green powder. On $SiO_2$ TLC it showed single spot in the solvent system—Chloroform:methanol:water (35:10:2 v/v) it was coded as K007.

K007 was crystallized with MeOH-$H_2O$ (9:1) as colourless plates. HPLC analysis indicated it to be a single compound.

The overall yield of the saponin was 26.5% based on n-butanol extract of the organism.

EXAMPLE-2

Aerial portion of *Chlorophytum-nimonii* (100 g) was extracted with ethanol as per example-1. The ethanolic extract (10.0 g) still consisted of some inorganic salts. This extract in methanol:Water ((1:1) was loaded on to Sephadex LH-20 column packed in methanol:water (9:1) and eluted with methanol:water (9:1 v/v). Fractions (25 ml) were collected and monitored on $SiO_2$-TLC plates using the solvent system (chloroform-methanol-water (35:10:2). First and last few fractions contained undesirable compounds and were therefore rejected. Fraction 5–10 contained saponin, which were combined and the solvent was removed to get a colourless residue yield (25 mg). It was crystallized as colourless solid. Overall yield was 22.5%.

EXAMPLE-3

Aqueous ethanolic extract (50%) was obtained from 100 g of the air-dried powder of aerial part of the plant *Chlorophytum-nimonii* as per example-1. The concentrated 50% aqueous ethanolic extract was dissolved in 500 ml of ethanol:water (3:1: v/v). The insoluble residue was rejected and the ethanol-water soluble portion was partitioned with chloroform (3×500 ml) followed by extraction with n-butanol (5×500 ml). The extract and ethanol:water concentrated powder still contained saponin and therefore extracted with butanol in a solid liquid extractor (soxhlet extractor) using n-butanol as a solvent.

The total combined butanol extract was dissolved in ethanol (100 ml) and to it ether was gradually added to precipitate the saponin. The precipitate was centrifuged and crystallized as while plates. The overall yield was 27.5%.

Avance DRVI, equipped with a 5 mm. Multinuclear Inverse probe head with z-shielded geiadieut, chemical shifts are given on the δ-scale and were referred to the solvent recurrence at (as) 2.49 ppm., for $^1$HNMR and 39.4 ppm. for carbon. The assignments of sugar units with their connectivity were analysed with the combination of COSY, TOCSY, HMQUC, and HMBC experiments. The $^{13}$CNMR spectrum consists of forty nine carbon signals. Spectral editing by DEPT experiments provided 5 methyl groups, 16 methylene groups and 30 methine groups.

In $^1$H spectrum, the down field region showed resonance of 5 anomeric signals at 5.12, 4.60, 4.43, 4.36 and 4.29 ppm. and their $^{13}$C signals were at 99.9, 104.0. 103.5, 103.6 and 98.4 ppm respectively; which were assigned by HMBC spectrum. Out of 5 anomeric signals one was α-in nature and other 4 were β in nature. The detailed assignments of sugars are summarized in Table-1. The anomeric signal at 5.12 ppm. of rhamnose showed a three bond correlation with C-3 of aglycone. In HMBC spectrum, H-4 of rhamnose showed contour peak with the anomeric carbon of glucose (d) at δ

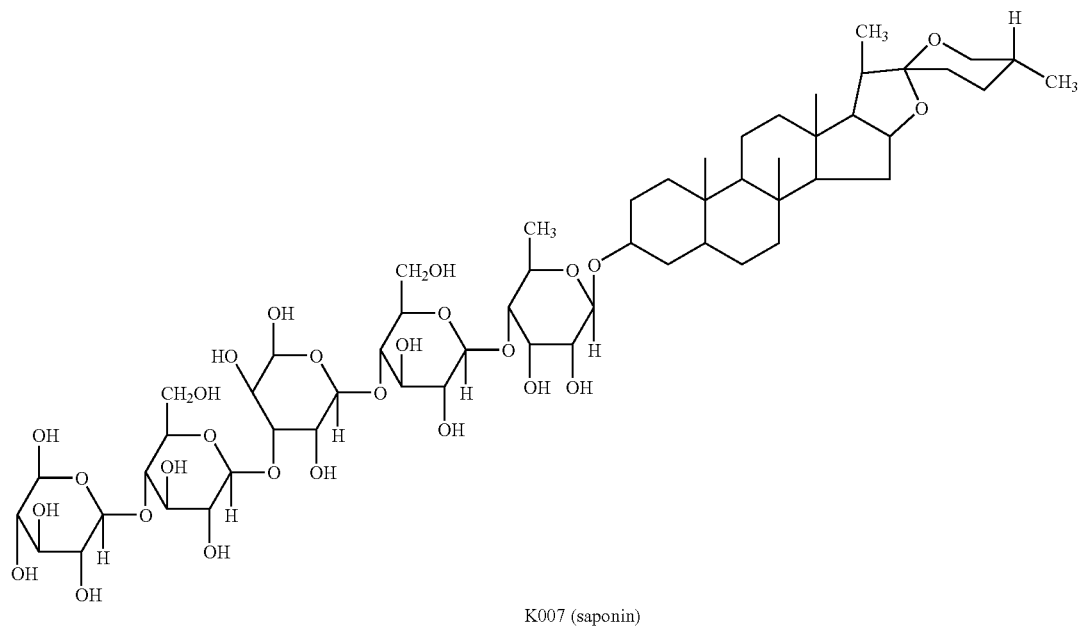

K007 (saponin)

Neotigogenin 3-o-α-L-rhamnopyranosly (1–4) β-D-glucopyranosyl (1–3) β-D-xylopyranosyl(1–4) β-D-glucopyranosyl (1–4) β-D-xylopyranoside.

Structure Determination: Saponin (Tigogenin penta glycoside).

NMR spectra were recorded in DMSO d$_6$ at room temperature on a 300 MHz FT NMR spectrometer (Brucker 104.0. In a similar way, H-3 of glucose showed a correlation of anomeric carbon of xylose (c) at 98.4 ppm. and H-4 of glucose (b) with the anomeric carbon of xylose (a) at 103.6 ppm. and which were further confirmed by the NOESY spectrum and the linkages of sugar units expressed in FIG. 1. NMR data of the Tigogenin penta glycoside sugar units are tabled (Table 5)

TABLE 5

| S. No. | Xyl (a)1H (13 C) | Glu (b) | Xyl (c) | Glu (d) | Rh (e) |
|---|---|---|---|---|---|
| 1. | 4.38 (103.6) | 4.29 (98.4) | 4.48 (103.5) | 4.60 104.0) | 5.12 (99.9) |
| 2. | 3.31 (69.5) | 3.31 (72.6) | 3.03 (73.5) | 3.31 (71.4) | 3.66 (70.6) |
| 3. | 3.39 (70.6) | 3.33 (73.5) | 3.11 (76.6) | 3.60 (85.7) | 3.39 (70.6) |
| 4. | 3.50 (74.4) | 3.76 (79.5) | 3.49 ((75.9) | 3.09 (69.0) | 3.18 (71.9) |
| 5. | 3.90, 3.40 (63.9) | 3.34 (75.8) | 3.09, 3.76 (63.9) | 3.22 (75.8) | 3.95 (68.1) |
| 6. |  | 3.37, 3.34 (61.5) |  | 3.71, 3.35 (59.3) | 17.7 (1.05) |

Advantages:

The main advantages of the present invention are—
(1) It is a new saponin designated as Tigogenin penta glycoside.
(2) This saponin is present in high yield in aerial parts of *Chlorophytum nimoni* (20–21%).
(3) The aerial part of the plant may conveniently been used without much damage to the plant, therefore it insures constant availability of the raw material.
(4) The isolated Saponin is stable at room temperature (25–30°).
(5) It is a free flowing powder.

We claim:

1. Tigogenin pentaglycoside of formula 1 isolated from aerial parts of *Chlorophytum nimonii*

Formula 1

2. A process for the isolation of a Tigogenin pentaglycoside of formula 1 from aerial parts of *Chlorophytum nimonii*, which process comprises the steps of:
  (i) soaking material comprising dried and chopped aerial parts of *Chlorophytum nimonii* in a polar solvent at a temperature in the range of 25 to 30° C. to obtain an extract;
  (ii) filtering the extract, followed by removal of the polar solvent until dryness under vacuo to obtain the compound of formula; and
  (iii) purifying the compound of formula 1

Formula 1

3. The process as claimed in claim 2 wherein the polar solvent used is selected from the group consisting of butanol, methanol, ethanol, water and any mixture thereof.

4. The process as claimed in claim 2 wherein the dried and chopped aerial parts of *Chlorophytum nimonii* is are soaked up to 4 to 5 times in the polar solvent.

5. The process as claimed in claim 2 wherein the soaking is carried out for a period of about 24 hours.

6. The process as claimed in claim 2 wherein the filtrate is concentrated to 300 ml under reduced pressure below 50° C.

7. The process as claimed in claim 2 wherein the polar solvent used is 95% ethanol.

8. The process as claimed in claim 2 wherein the extract obtained at the end of step (ii) is subjected to fractionation into four fractions comprising hexane soluble fraction, n-butanol soluble fraction, chloroform soluble fraction and n-butanol insoluble fraction.

9. A pharmaceutical composition comprising a an amount of a compound of formula 1

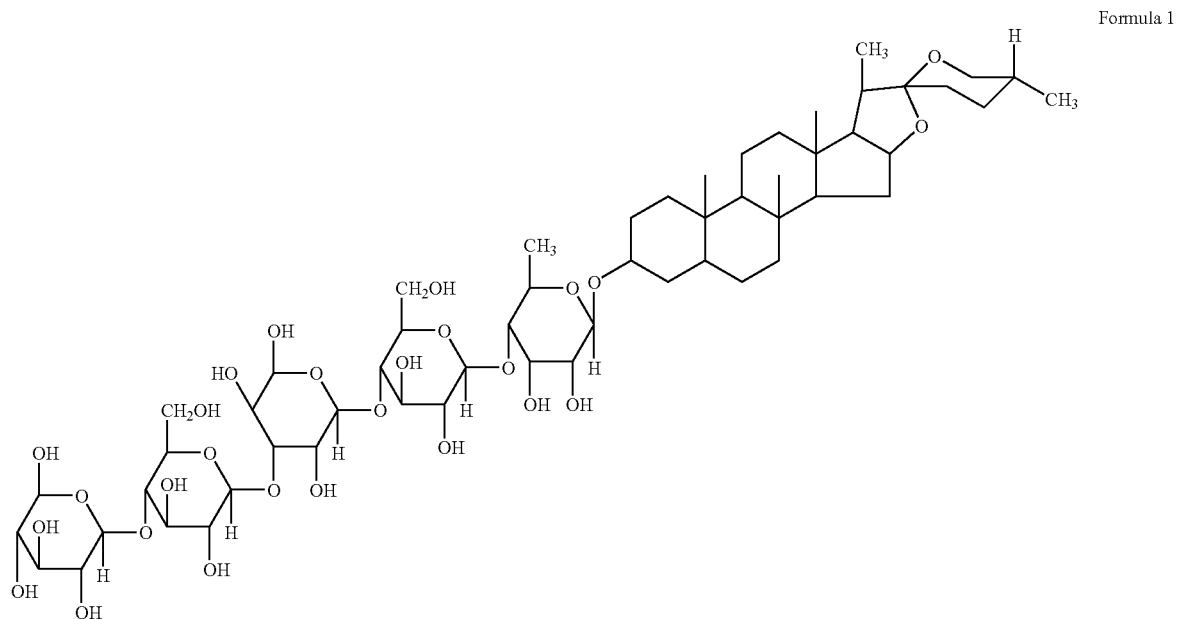

Formula 1 and one or more pharmaceutically acceptable additives.

10. The composition as claimed in claim 9 wherein the effective amount of the compound of formula 1 is in the range of 100 to 500 mg/kg of body weight of a patient.

11. A method for treating diabetes or hyperlipidemia comprising administering an effective amount of a compound of formula 1

Formula 1

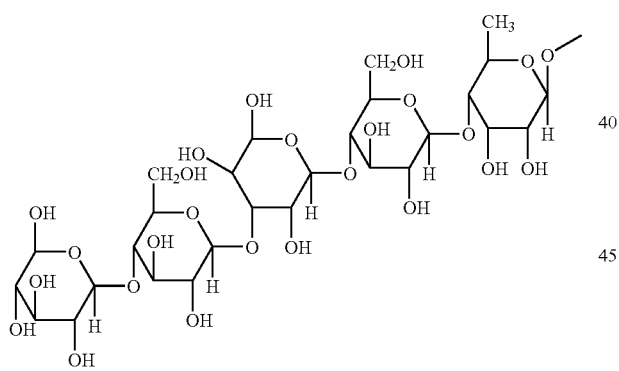

-continued

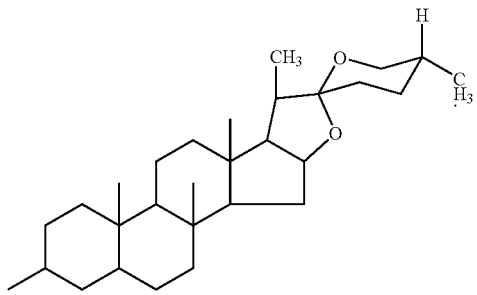

to a patient in need thereof.

* * * * *